(12) United States Patent
Allard et al.

(10) Patent No.: US 6,245,074 B1
(45) Date of Patent: Jun. 12, 2001

(54) ORTHOPAEDIC GLENOID REAMER

(75) Inventors: Randall N. Allard, Plymouth; John E. Meyers, Columbia City, both of IN (US)

(73) Assignee: Bristol-Myers Squibb Co., New York, NY (US)

( * ) Notice: Subject to any disclaimer, the term of this patent is extended or adjusted under 35 U.S.C. 154(b) by 0 days.

(21) Appl. No.: 09/388,136

(22) Filed: Sep. 1, 1999

(51) Int. Cl.$^7$ .................................................. A61B 17/14
(52) U.S. Cl. ............................................................ 606/80
(58) Field of Search ............................. 606/80, 180, 81; 407/53, 54; 408/199, 204, 200

(56) References Cited

U.S. PATENT DOCUMENTS

| | | | |
|---|---|---|---|
| 1,923,177 | * 8/1933 | Tucker | 606/80 |
| 3,412,733 | * 11/1968 | Ross | 606/81 |
| 4,011,025 | * 3/1977 | Kress | 408/153 |
| 4,023,572 | * 5/1977 | Weigand et al. | 606/81 |
| 4,199,284 | * 4/1980 | Kress et al. | 408/233 |
| 4,239,427 | * 12/1980 | Walton, II | 408/213 |
| 5,092,719 | * 3/1992 | Zsiger | 408/213 |
| 5,203,653 | * 4/1993 | Kudla | 606/81 |
| 5,376,092 | * 12/1994 | Hein et al. | 606/81 |
| 5,658,290 | * 8/1997 | Lechot | 606/80 |
| 5,709,688 | * 1/1998 | Salyer | 606/81 |
| 5,755,719 | * 5/1998 | Frieze et al. | 606/81 |
| 5,976,148 | * 11/1999 | Charpenet et al. | 606/81 |
| 6,045,302 | * 4/2000 | Orr | 408/200 |

OTHER PUBLICATIONS

Global™ Total Shoulder Arthroplasty System Design Rationale and Surgical Technique; 1992 DePuy.

Kirschner Integrated Shoulder System™ Surgical Technique; Biomet, Inc. Published 1995.

The Neer II Total Shoulder System; the 3M™ Modular Shoulder System Surgical Technique; Published 1995.

* cited by examiner

Primary Examiner—Gene Mancene
Assistant Examiner—Eduardo C. Robert

(57) ABSTRACT

An orthopaedic reamer includes an elongate shaft and a cutting head attached to an end of the shaft. The cutting head has a diameter which is larger than the shaft. The cutting head has a radial perimeter and an axial cutting face with a plurality of cutting teeth. The cutting head has at least one visualization groove which extends radially inward from the radial perimeter. The at least one visualization groove allows a surgeon to visualize the cut bone during surgery.

5 Claims, 6 Drawing Sheets

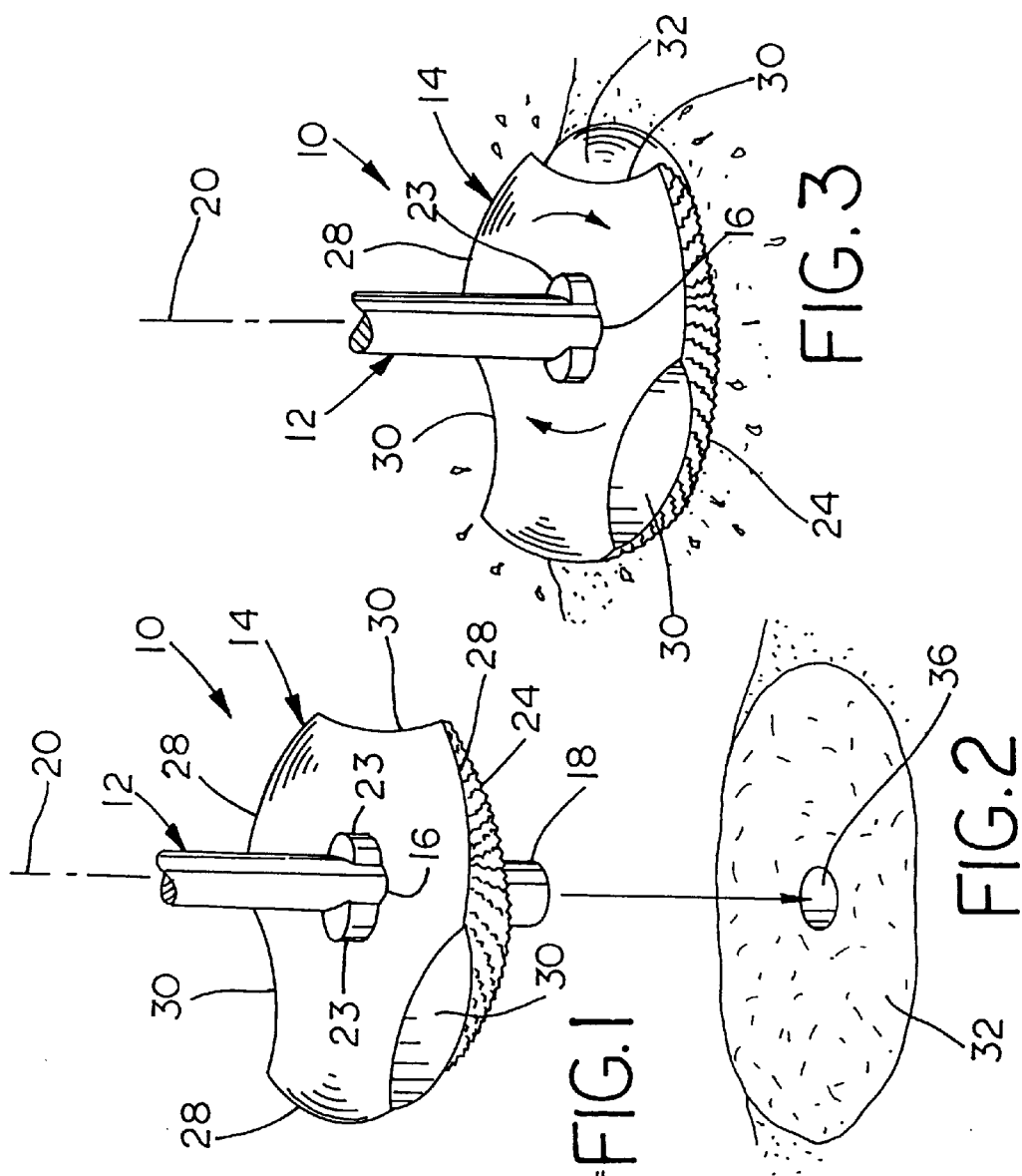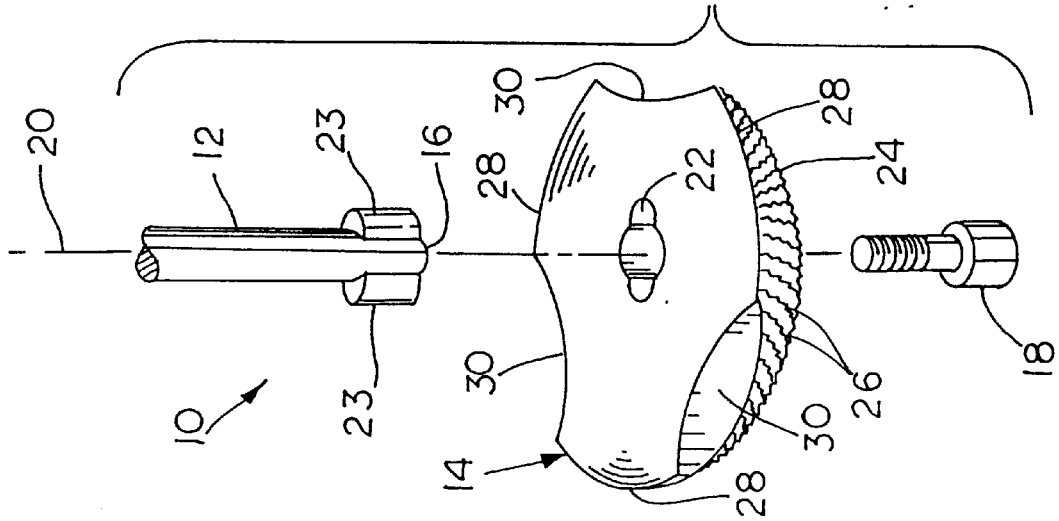

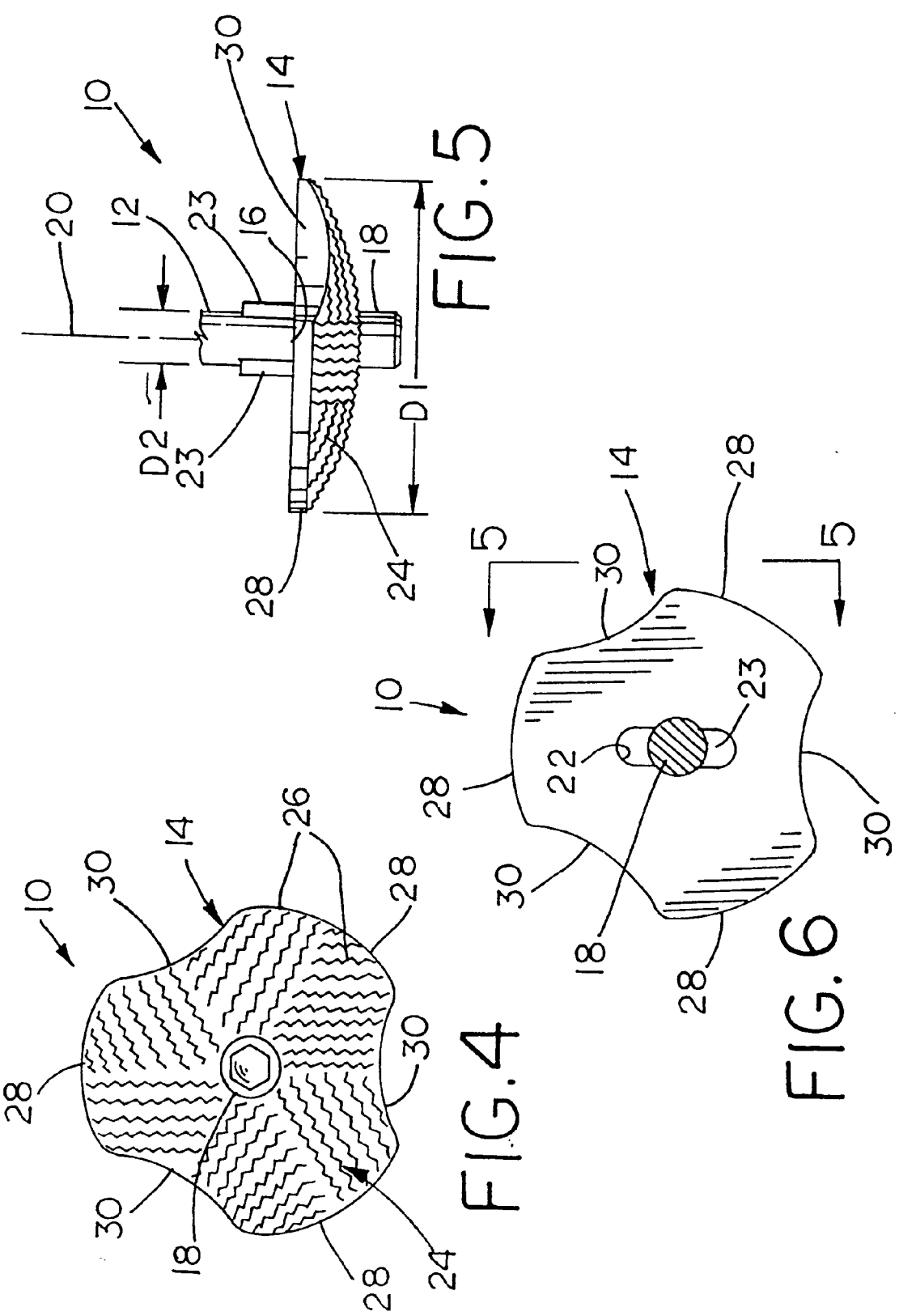

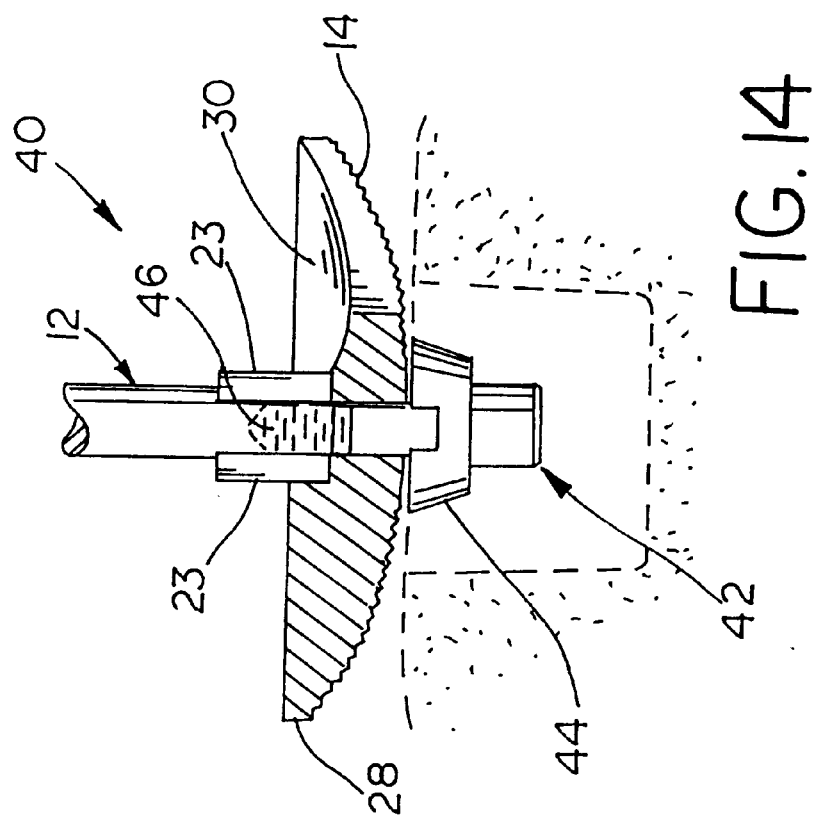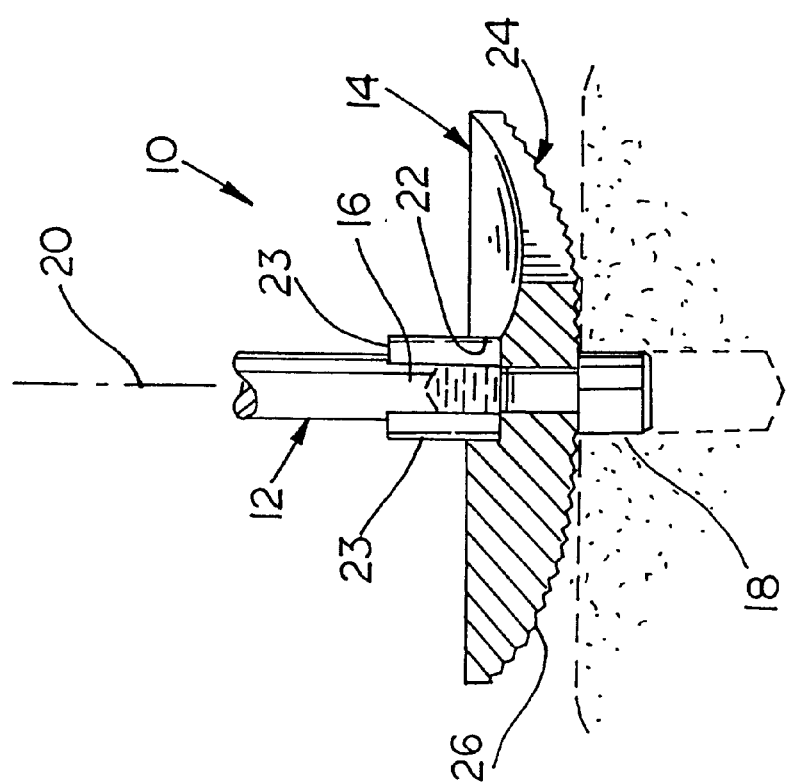

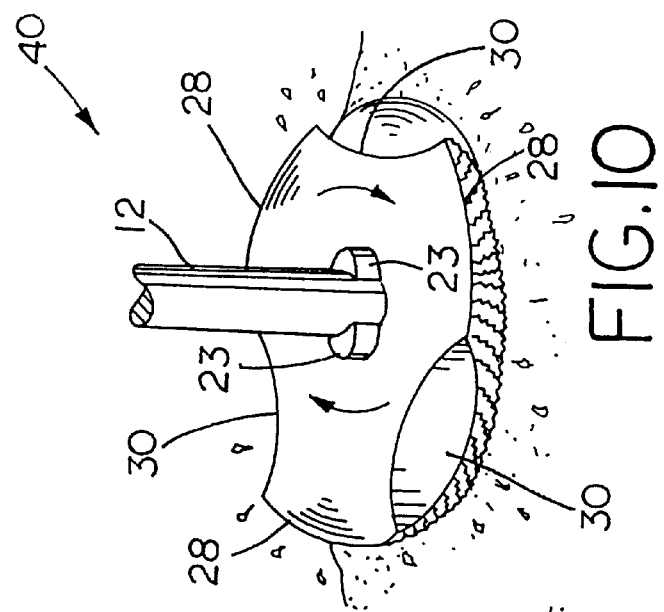
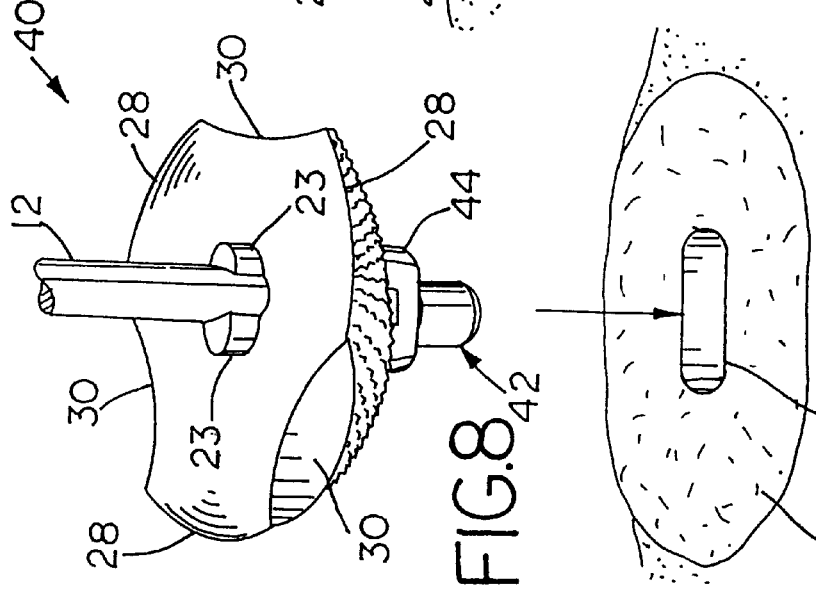
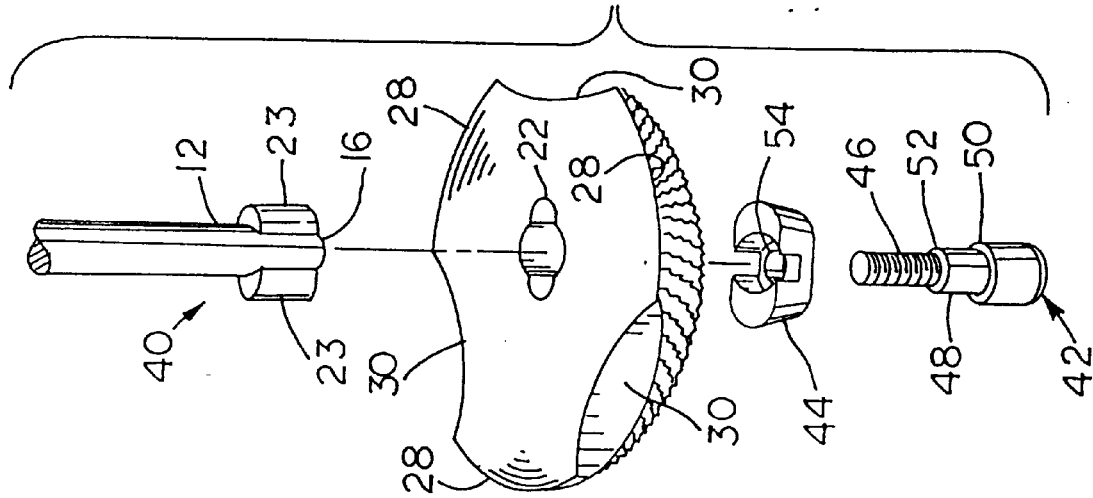

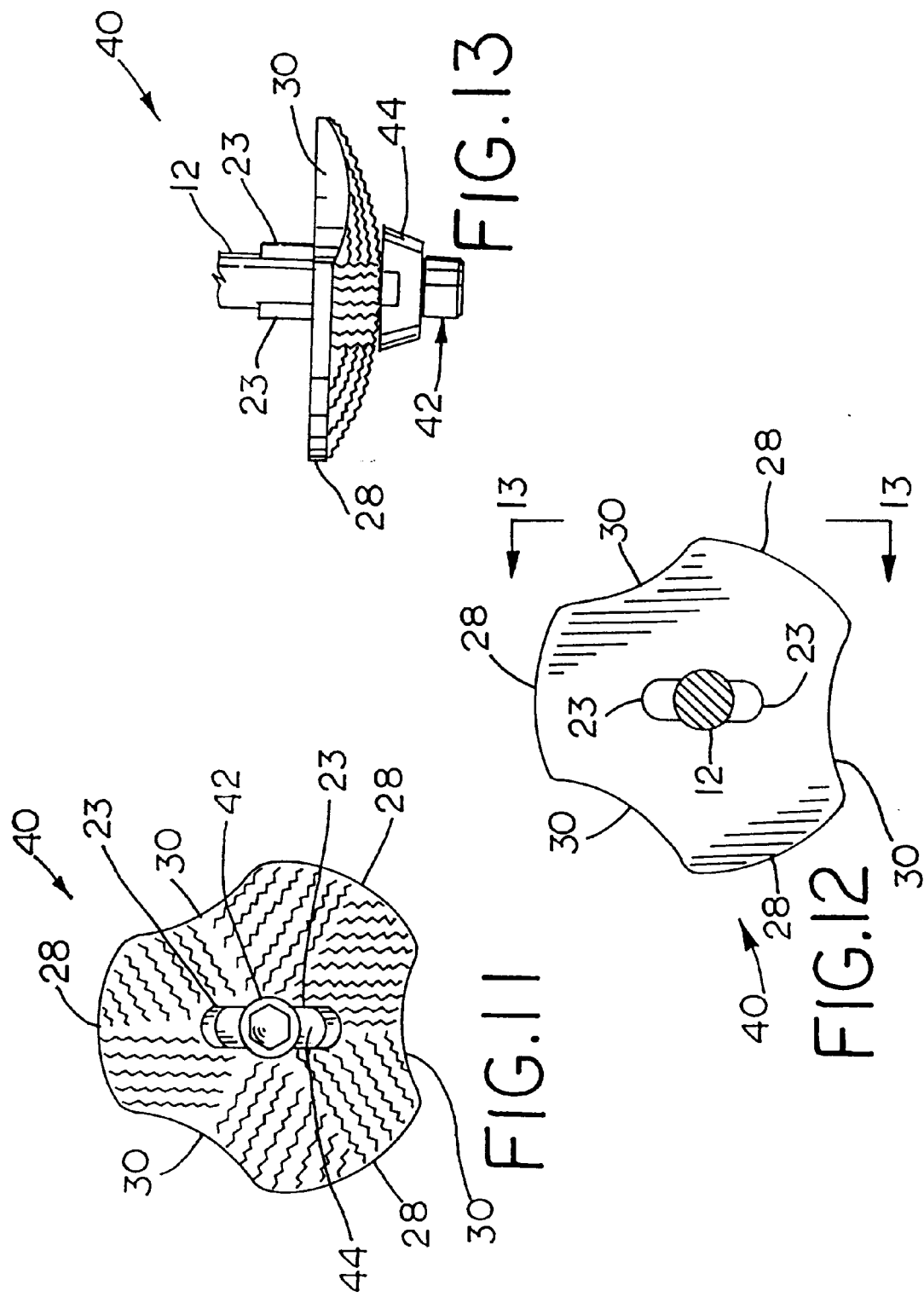

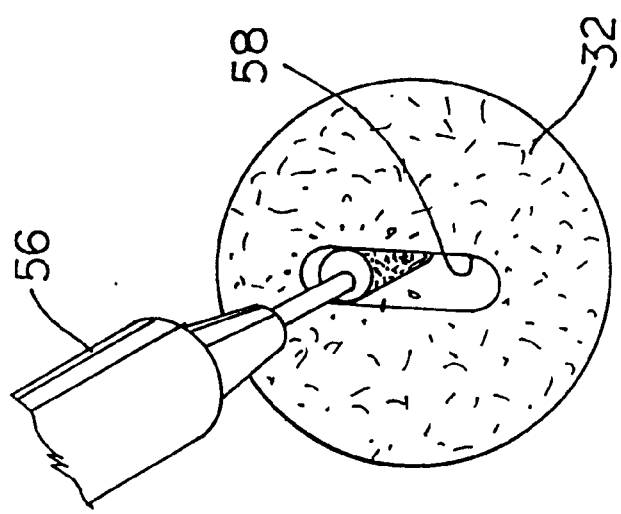
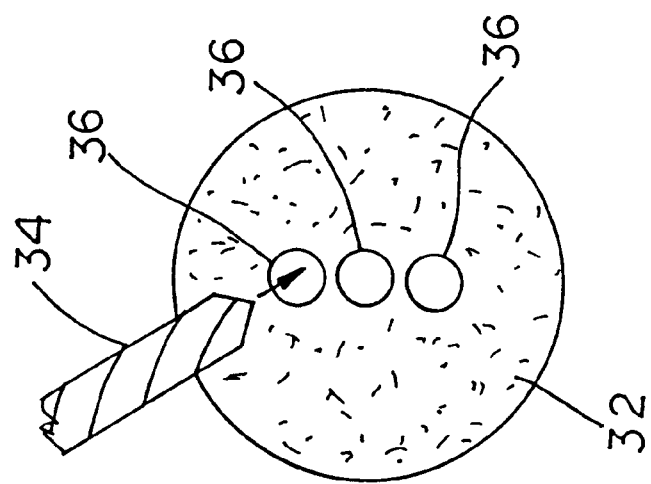
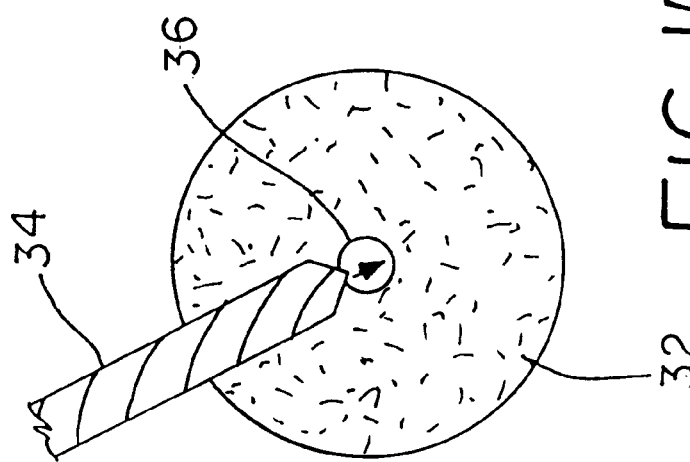

ORTHOPAEDIC GLENOID REAMER

BACKGROUND OF THE INVENTION

1. Field of the Invention

The present invention relates to orthopaedic instrumentation, and, more particularly, to an orthopaedic reamer used to prepare a bone for receiving an implant.

2. Description of the Related Art

An orthopaedic reamer is used to prepare a bone for receiving an orthopaedic implant. For example, a glenoid reamer may include an elongate shaft which is attached to a cutting head. The cutting head may include an axial cutting face with a plurality of cutting teeth. The cutting head has a substantially constant radial perimeter. The surgeon places the cutting head against the glenoid surface and rotates the reamer using an external rotatable drive source such that the cutting teeth rotate to form the glenoid surface. Since the cutting head is of a substantially constant uniform diameter, the surgeon typically removes a relatively small amount of bone, and moves the cutting head away from the glenoid surface to inspect the cut surface. If additional bone must be removed, it is necessary for the surgeon to again insert the cutting head through the opening formed in the soft tissue and against the glenoid surface to be cut. This process of cutting the glenoid surface, moving the cutting head away from the glenoid surface, inspecting the glenoid surface, and reinserting the cutting head for additional cutting is time consuming.

What is needed in the art is a glenoid reamer which allows a surgeon to adequately inspect the glenoid surface during a cutting operation without removing the reamer from the bone.

SUMMARY OF THE INVENTION

The present invention provides an orthopaedic glenoid reamer having a cutting head with a plurality of visualization slots which extend radially inward from a radial perimeter to allow a surgeon to visualize a cut bone surface during surgery.

The invention comprises, in one form thereof, an orthopaedic reamer including an elongate shaft and a cutting head attached to an end of the shaft. The cutting head has a diameter which is larger than the shaft. The cutting head has a radial perimeter and an axial cutting face with a plurality of cutting teeth. The cutting head has at least one visualization groove which extends radially inward from the radial perimeter. The at least one visualization groove allows a surgeon to visualize the cut bone during surgery.

An advantage of the present invention is that the reamer does not have to be removed from the glenoid surface for the surgeon to inspect the cut bone surface.

Another advantage is that the visualization grooves in the cutting head may have different configurations and still allow adequate visualization of the cut bone surface.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is an exploded, perspective view of an embodiment of an orthopaedic glenoid reamer of the present invention;

FIG. 2 is a perspective view of the glenoid reamer of FIG. 1 being positioned against a glenoid surface;

FIG. 3 is a perspective view of the glenoid reamer of FIGS. 1 and 2 against a glenoid surface;

FIG. 4 is an end view of the glenoid reamer of FIGS. 1–3;

FIG. 5 is a side view of the glenoid reamer of FIGS. 1–4;

FIG. 6 is an opposing end view of the glenoid reamer of FIGS. 1–5;

FIG. 7 is a side, sectional view of the glenoid reamer of FIGS. 1–6;

FIG. 8 is an exploded, perspective view of another embodiment of an orthopaedic glenoid reamer of the present invention;

FIG. 9 is a perspective view of the glenoid reamer of FIG. 8 being positioned relative to a glenoid surface;

FIG. 10 is a perspective view of the glenoid reamer of FIGS. 8 and 9 against a glenoid surface;

FIG. 11 is an end view of the glenoid reamer of FIGS. 8–10;

FIG. 13 is a side view of the glenoid reamer of FIGS. 8–11;

FIG. 12 is an opposing end view of the glenoid reamer of FIGS. 8–13;

FIG. 14 is a side, sectional view of the glenoid reamer of FIGS. 8–13 positioned relative to a glenoid surface;

FIG. 15 is a perspective view of a glenoid surface being prepared with a centrally located positioning hole; and FIGS. 16 and 17 are perspective views illustrating the formation of a locating slot within a glenoid surface.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Referring now to the drawings, and more particularly to FIGS. 1–7, there is shown an embodiment of an orthopaedic reamer 10 of the present invention, which generally includes an elongate shaft 12 and a cutting head 14. In the embodiment shown, orthopaedic reamer 10 is in the form of a glenoid reamer.

Elongate shaft 12 includes an end 16 which is attached to cutting head 14. In the embodiment shown, end 16 is internally threaded and receives a threaded fastener 18 which extends through cutting head 14. Shaft 12 also includes an opposite end (not shown) which may be attached to a suitable rotational drive source, such as an electric motor attached to an appropriate gear drive Shaft 12 is rotatably driven about a longitudinal axis 20 thereof.

Cutting head 14 includes a centrally positioned attachment slot 22 which receives corresponding radially extending keys 23 of shaft 12 to prevent relative rotational movement between cutting head 14 and shaft 12. Cutting head 14 has a diameter D1 (FIG. 5) which is larger than a diameter D2 of shaft 12. Cutting head 14 has an axial cutting face 24 with a plurality of cutting teeth 26. Cutting teeth 26 may have any suitable configuration, such as straight, fluted, serrated, etc.

Cutting head 24 also has a radial perimeter 28 which defines diameter D1. A plurality of visualization grooves 30 extend radially inward from radial perimeter 28 and allow a surgeon to visualize a cut bone surface during surgery to determine if the bone surface has been properly prepared or if additional cutting is needed. Visualization grooves 30 also allow cut bone chips to be removed from the bone surface being cut.

In the embodiment shown, visualization grooves 30 are configured as three generally semi-circular shaped grooves (or scallops) which extend radially inward from radial perimeter 28 The semi-circular shape of visualization grooves 30 allows a sufficient amount of bone to be seen during surgery so that the surgeon can determine whether additional cutting is required. In addition, the semi-circular shape of visualization grooves 30 allows sufficient additional structure defining radial perimeter 28 to carry the plurality of cutting teeth 26. Visualization grooves 30 may have other cross sectional shapes when viewed in an axial direction, such as rectangular, triangular, etc. Visualization Grooves 30 are substantially equi-angularly spaced about radial perimeter 28 in the embodiment shown. Each visualization groove 30 extends approximately one-third the distance from diameter D1 toward longitudinal axis 20. Each visualization groove 30 may extend a larger amount (e.g., one-half) the distance between radial perimeter 28 and longitudinal axis 20, dependent on the specific circumstances.

During use, the shoulder of the patient is properly prepared such that the glenoid surface 32 is exposed (FIGS. 2 and 15). For example, the shoulder muscles may be moved away from glenoid surface 32 and a drill 34 used to form a centrally located hole 36 therein. Hole 36 acts as a pilot hole for positioning reamer 10 relative to glenoid surface 32. The axially projecting portion of fastener 18 is inserted into hole 36 in glenoid surface 32. Cutting head 14 of glenoid reamer 10 is then placed against the glenoid surface for preparing the glenoid to receive an implant. Shaft 12 and cutting head 14 are rotated using a suitable rotatable drive source (not shown) at a desired rotational speed. The surgeon then deactuates the rotatable drive source such that reamer 10 stops rotating, while at the same time maintaining cutting head 14 against the glenoid surface 32 being formed. The surgeon visualizes the cut bone surface through the cavities defined by visualization grooves 30. If the cut bone surface appears to be adequately formed, the surgeon may simply move glenoid reamer 10 away from the glenoid surface in an axial direction. Otherwise, the rotatable drive source is again actuated and additional bone is removed. This process of removing bone and visualizing the cut bone surface is repeated until an implant receiving glenoid surface is properly formed. Glenoid reamer 10 is then moved away from the glenoid surface in an axial direction for receiving the bone cement and/or glenoid implant.

Referring now to FIGS. 8–14 and 16–17, there is shown another embodiment of a reamer 40 of the present invention which includes a shaft 12 and cutting head 14 the same as the embodiment of reamer 10 shown in FIGS. 1–7. However, reamer 40 includes a fastener 42 which is configured differently than fastener 18 of reamer 10, and a positioning lug 44 which is positioned within a corresponding slot formed in glenoid surface 32. Fastener 42 includes a male threaded portion 46 which threadingly engages with a female threaded portion in end 16 of shaft 12. Fastener 18 also includes a non-threaded carrier portion 48 which has a diameter larger than threaded portion 46 and defines shoulders 50 and 52 When fastener 42 is engaged with shaft 12, shoulder 52 abuts against end 16.

Positioning lug 44 has an opening 54 with an inside diameter which is larger than the outside diameter of carrier portion 48 of fastener 42. Lug 44 also has a height which is less than the height of carrier portion 48. Thus, when fastener 42 is engaged with shaft 12, lug 44 is free to rotate about carrier portion 48.

During use, reamer 40 may be used either in conjunction with or in place of reamer 10. Glenoid surface 32 is prepared for use with reamer 40 by forming an elongate slot within glenoid surface 32 which receives lug 44. Drill 34 may be used to form a plurality of aligned holes in glenoid surface 32, such as the three holes 36 shown in FIG. 16. A grinding bit 56 or the like may be used to form an elongate slot 58 in glenoid surface 32 by removing bone to connect the three holes 36. Slot 58 has a width which is just slightly larger than the width of lug 44 and a length which is greater than the length of lug 44. The length of slot 58 may generally correspond to the length of a keel extending from the back side of a glenoid implant (not shown) which is implanted within glenoid surface 32. Reamer 40 is placed against glenoid surface 32, such that fastener 42 and lug 44 are received within slot 58 and cutting head 14 is placed against glenoid surface 32 (FIG. 14). Shaft 12 and cutting head 14 are then rotated using a suitable drive source (not shown) at a desired rotational speed. As cutting head 14 rotates, lug 44 remains stationary relative to cutting head 14. The surgeon then moves cutting head 14 such that lug 44 slides within slot 58 in generally parallel directions relative to the longitudinal extension of slot 58. Thus, reamer 40 forms glenoid surface with a generally oblong shape for receipt of the glenoid implant (not shown). To determine whether glenoid surface 32 has been properly prepared, the surgeon deactuates the rotatable drive source such that reamer 10 stops rotating while at the same time maintaining cutting head 14 against glenoid surface 32. The surgeon visualizes the cut bone surface through the cavities defined by visualization grooves 30. If the cut bone surface appears to be adequately formed, the surgeon may simply remove glenoid reamer 40 away from the glenoid surface 32 in an axial direction. Otherwise, the rotatable drive source is again actuated and additional bone is removed. This process of removing bone and visualizing the cut bone surface is repeated until an implant receiving glenoid surface is properly formed. Glenoid reamer 40 is then moved away from the glenoid surface in an axial direction for receiving the bone cement and/or glenoid implant.

In the embodiments of reamers 10 and 40 shown and described above, glenoid surface 32 is described as being formed with reamer 10 or reamer 40. However, it is to be understood that reamers 10 and 40 may be used together to form glenoid surface 32. That is, reamer 10 may be placed within a single hole 36 and used to form glenoid surface 32. Thereafter, glenoid surface 32 may be formed with a slot 58. Reamer 40 may then be used to form an oblong shaped prepared surface of glenoid surface 32.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer, comprising:
   an elongate shaft having a diameter; and
   a cutting head attached to an end of said shaft and having a diameter which is larger than said shaft diameter, said cutting head having a radial perimeter and an axial cutting face with at least one cutting tooth, said cutting head having at least one visualization groove extending radially inward from said radial perimeter, wherein said shaft has a longitudinal axis, and wherein each said visualization groove extends between approximately one-third and one-half the distance from said radial perimeter toward said longitudinal axis.

2. An orthopaedic reamer, comprising:

an elongate shaft having a diameter; and a cutting head attached to an end of said shaft and having a diameter which is larger than said shaft diameter, said cutting head having a radial perimeter and an axial cutting face with at least one cutting tooth, said cutting head having at least one visualization groove extending radially inward from said radial perimeter, wherein said cutting head has a centrally positioned attachment slot, and wherein said shaft end is positioned within said slot.

3. An orthopaedic reamer, comprising:

an elongate shaft having a diameter; and a cutting head attached to an end of said shaft and having a diameter which is larger than said shaft diameter, said cutting head having a radial perimeter and an axial cutting face with at least one cutting tooth, said cutting head having at least one visualization groove extending radially inward from said radial perimeter, further comprising a fastener attached to said elongate shaft and a lug carried by said fastener, said lug positioned adjacent said axial cutting face and rotatable relative to said cutting head.

4. A method of preparing a bone to receive an orthopaedic implant, comprising the steps of:

providing an orthopaedic reamer with an elongate shaft, the shaft having a diameter, and a cutting head attached to an end of said shaft, said cutting head having a diameter which is larger than said shaft diameter, said cutting head having a radial perimeter and an axial cutting face with at least one cutting tooth, said cutting head having at least one visualization groove extending radially inward from said radial perimeter;

placing said cutting head against said bone;

rotating said cutting head such that said at least one cutting tooth cuts said bone;

stopping said rotation of said cutting head with said cutting head against said bone; and visualizing said cut bone through at least one said visualization groove.

5. The method of claim 4, wherein said bone comprises a glenoid.

* * * * *